United States Patent [19]

Hayashida et al.

[11] Patent Number: 5,021,563

[45] Date of Patent: Jun. 4, 1991

[54] METAL NAPHTHALOCYANINE DERIVATIVE AND PROCESS FOR PRODUCING THE SAME

[75] Inventors: Shigeru Hayashida; Seiji Tai; Nobuyuki Hayashi; Yasushi Iwakabe; Noriyuki Kinjo; Shunichi Numata, all of Hitachi, Japan

[73] Assignees: Hitachi Chemical Company, Ltd.; Hitachi, Ltd., both of Tokyo, Japan

[21] Appl. No.: 418,087

[22] Filed: Oct. 6, 1989

Related U.S. Application Data

[62] Division of Ser. No. 147,694, Jan. 25, 1988, Pat. No. 4,886,721.

[30] Foreign Application Priority Data

Jan. 29, 1987 [JP] Japan ................................ 62-19155

[51] Int. Cl.[5] .................... C09B 47/04; C07D 257/00; G11B 7/24; B21M 5/26

[52] U.S. Cl. .................................................. 540/128

[58] Field of Search .......................... 540/128; 430/59

[56] References Cited

U.S. PATENT DOCUMENTS

| | | | |
|---|---|---|---|
| 3,094,535 | 6/1963 | Kenney et al. | 540/128 |
| 4,131,609 | 12/1970 | Wynne et al. | 540/128 |
| 4,132,842 | 1/1979 | Wynne et al. | 540/128 |
| 4,492,750 | 1/1985 | Law et al. | 430/945 |
| 4,557,989 | 12/1985 | Branston et al. | 430/59 |
| 4,725,525 | 2/1988 | Kenney et al. | 430/964 |
| 4,749,637 | 6/1988 | Hayashida et al. | 430/78 |
| 4,766,054 | 8/1988 | Hirose et al. | 430/945 |
| 4,833,264 | 5/1989 | Tai et al. | 558/416 |
| 4,927,735 | 5/1990 | Era et al. | 540/128 |

FOREIGN PATENT DOCUMENTS

| | | | |
|---|---|---|---|
| 0191215 | 8/1986 | European Pat. Off. . | |
| 58-158649 | 9/1983 | Japan . | |
| 61-177287 | 8/1986 | Japan . | |
| 61-177288 | 8/1986 | Japan . | |
| 62-53809 | 7/1987 | Japan | 540/128 |

OTHER PUBLICATIONS

Wheeler et al., JACS 1989, 106, 7404–7410.

*Primary Examiner*—Mark L. Berch
*Assistant Examiner*—Edward C. Ward
*Attorney, Agent, or Firm*—Frishauf, Holtz, Goodman & Woodward

[57] ABSTRACT

A metal naphthalocyanine derivative and process for producing said derivative which is represented by the following formula (I):

(I)

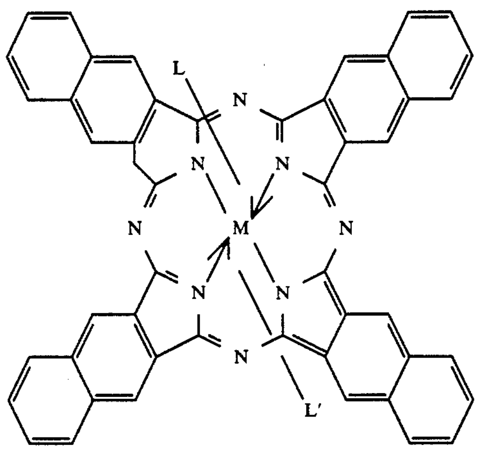

wherein M represents germanium or tin; L and L' each independently represent a halogen, a hydroxyl group, an alkyl group, an alkoxy group or a siloxy group of the formula $R_1R_2R_3SiO$— (wherein $R_1$, $R_2$ and $R_3$ each independently represent a hydrogen atom, an alkyl group, an alkoxy group or an aryl group).

10 Claims, 10 Drawing Sheets

METAL NAPHTHALOCYANINE DERIVATIVE AND PROCESS FOR PRODUCING THE SAME

This is a division of application Ser. No. 07/147,694 filed Jan. 25, 1988, Pat. No. 4,886,721.

BACKGROUND OF THE INVENTION

This invention relates to an electrophotographic plate utilizing a specific metal naphthalocyanine derivative, and also relates to a derivative described above and a process for producing the same.

In recent years, with the advent of laser diodes, films containing compounds having sensitivity to longer wavelengths which is the wavelength of laser diodes have been actively developed for utilization for photoconductive layers of electrophotographic plate, photosensitive layers of recording media, display layers of electrochromic display members, electrode layers of photocatalytic electrode reactions, photosensitive layers of chemical sensors, luminescent layers of electroluminescence, etc.

For example, to describe about electrophotographic plates, as the electrophotographic plates of the prior art, there is one in which selenium (Se) film with a thickness of about 50 μm is formed by the vacuum vapor deposition method on an electoconductive substrate such as aluminum, etc.

However, such Se electrophotographic plate has the problem that it has only sensitivity to wavelengths up to around 500 nm, etc. Also, there is an electrophotographic plate having Se layer with a thickness of about 50 μm on an electroconductive substrate, and further an alloy layer of selenium-tellurium (Se-Te) with a thickness of several μm formed thereon. However, while on one hand such electrophotographic plate can be extended in spectral sensitivity to longer wavelengths as the content of Te in the above Se-Te alloy is increased, on the other hand, surface charges retention properties deteriorate with an increase in the amount of Te added, whereby there is the serious problem that it no longer useful as the electrophotographic plate.

Also, there is the so called complex double layer type electrophotographic plates produced by forming a charge generation layer on an aluminum substrate by coating chlorocyan blue or squarilium acid derivative with a thickness of about 1 μm and forming a charge transport layer thereon by coating a polyvinylcarbazole having high insulation resistance or high insulation resistance mixture of pyrazoline derivative and a polycarbonate in 10 to 20 μm thickness, but such electrophotographic plates have practically no sensitivity to a light having a wavelength of 700 nm or more.

Further, in the complex double layer type electrophotographic plate, there is also an electrophotographic plate improved in the above drawback, namely having sensitivity to around 800 nm which is laser diode oscillation region in many of these electrophotographic plates, a charge generation layer comprising a thin film with a thickness of about 1 μm of a metal phthalocyanine having a metal of the group III or the group IV of the periodic table as the center metal is formed by the vacuum vapor deposition method and thereafter is dipped in a shifting agent solution or contacted with the vapor thereof, thereby to shift the absorption band which is inherently around 700 nm to around 800 nm and to impart longer wavelength sensitivities to the electrophotographic plate.

A complex double layer type electrophotographic plate is formed by forming a charge transport layer on the above charge generation layer by coating with a polyvinylcarbazole having high insulation resistance or a high insulation resistance mixture of a hydrazone derivative or pyrazoline derivative and a polycarbonate or a polyester in 10 to 20 μm thickness. However, in this case, the metal phthalocyanine thin film having a metal of the group III or the group IV of the periodic table as the center metal used as the charge generation layer has essentially no absorption at around 800 nm of the laser diode oscillation region, and there is involved the serious problem that the electrophotographic plate formed by use of this thin film has little or no sensitivity to the light of around 800 nm unless it is treated with a shifting agent (see Japanese Unexamined patent Publication No. 158649/1983).

In laser beam printers by use of an electrophotographic plate having a photoconductive layer, various attempts have been made in recent years to employ a laser diode as the light source, and also developments of films excellent in sensitivity to laser beam have been variously made in other uses. In this case, since the wavelength of said light source is around 800 nm, it is strongly demanded to produce a film which can absorb longer wavelength light of around 800 nm to be converted efficiently to another energy. Also, in the electrochromic display,, a film (display layer) capable of being changed in color by efficient electrical redox has been demanded.

Whereas, an information recording medium and an optical information recording medium using a naphthalocyanine derivative are proposed in Japanese Unexamined Patent Publications Nos. 177287/1986 and 177288/1986, but in these publications, there is no description about use of said naphthalocyanine derivative for an electrophotographic plate characterized by achieving recording through charging, exposure and developing.

SUMMARY OF THE INVENTION

The present invention provides an electrophotographic plate comprising a photoconductive layer containing an organic photoconductive substance on an electroconductive support, characterized in that said photoconductive layer has a film containing as the organic photoconductive substance a metal naphthalocyanine derivative represented by the formula (I):

(I)

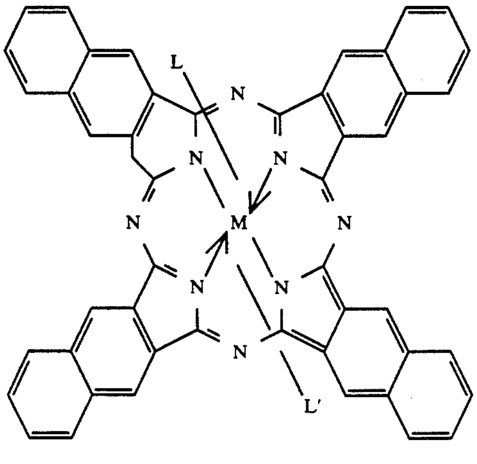

wherein M represents germanium or tin; L and L′ each independently represent a halogen, a hydroxyl group, an alkyl group, an alkoxy group or a siloxy group of the formula $R_1R_2R_3SiO$- (wherein $R_1$, $R_2$ and $R_3$ each independently represent a hydrogen atom, an alkyl group, an alkoxy group or an aryl group).

The present invention also provides a metal naphthalocyanine derivative defined above and a process for producing the same.

DETAILED DESCRIPTION OF THE INVENTION

Figure 1:
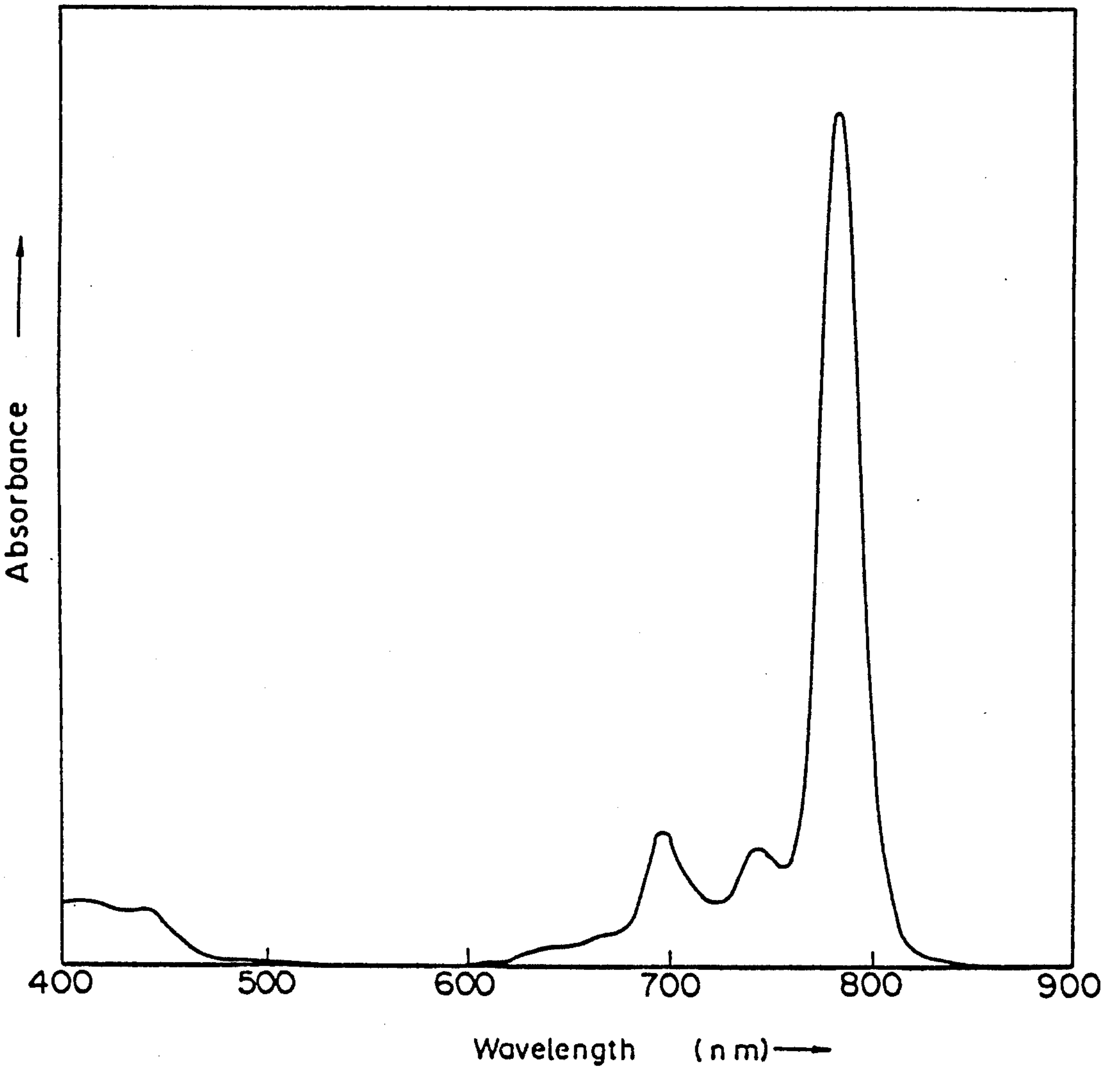
FIG. 1 is an absorption spectrum of the $CH_2Cl_2$ solution of the naphthalocyanine derivative synthesized in Synthesis example 1 wherein two triethylsiloxy groups are bonded to germanium which is the center metal.

The metal naphthalocyanine derivative to be used in the present invention, when L and L′ are other than halogen and hydroxyl group, can be most generally obtained by the reaction between the metal naphthalocyanine derivative of the formula (I) wherein L and/or L′ are hydroxyl groups and a compound corresponding to the group which can be bonded to the center metal germanium or tin. Specific synthetic methods of the metal naphthalocyanine derivative of the present invention are shown below.

By reacting 1,3-diiminobenz(f)isoindoline with germanium tetrachloride or stannic chloride at about 210° C. for about 2.5 hours, a metal naphthalocyanine derivative of the formula (I) wherein L and L′ are chlorine atoms can be synthesized. Subsequently, by acid treatment or alkali treatment of this derivative, two chlorine atoms can be substituted with hydroxyl groups to obtain a metal naphthalocyanine derivative of the formula (I) wherein L and L′ are hydroxyl groups. Next, by reacting this derivative with alcohol or $R_1R_2R_3SiCl$ or $R_1R_2R_3SiOH$ at 140° to 150° C. for about 1.5 hours, a germanium or tin naphthalocyanine compound wherein L and L′ are alkoxy groups or siloxy groups can be synthesized.

In the formula (I), the metal naphthalocyanine derivative in which one of L and L′ is an alkyl group is prepared by reacting 1,3-diiminobenz(f)isoindoline with $RSiCl_3$ (R is an alkyl group) at about 210° C. for about 2.5 hours to synthesize a metal naphthalocyanine in which one of L and L′ is a chlorine atom and the other is an alkyl group. This derivative may be also used as the metal naphthalocyanine derivative of the present invention. Next, by treating this derivative according to the method as described above, a derivative in which the other of L and L′ is a hydroxyl group, an alkoxy group or a siloxy group can be synthesized.

In the formula (I), the metal naphthalocyanine derivative wherein L and L′ are alkyl groups can be obtained by reacting 1,3-diiminobenz(f)isoindoline with $R'R''SiCl_2$ (wherein R′ and R″ are respectively alkyl groups) at about 210° C. for about 2.5 hours.

Concerning L and L′ in the formula (I), the halogen may include chlorine, bromine, fluorine the like; the alkyl group may include methyl, ethyl, propyl, butyl, hexyl groups and the like; the alkoxy group may include methoxy, ethoxy, propoxy, butoxy, pentoxy, hexoxy, heptoxy, octoxy, decoxy, dodecoxy, tetradecoxy, hexadecoxy, octadecoxy groups and the like; the siloxy group may include dimethylsiloxy, trimethylsiloxy, trimethoxysiloxy, dimethoxymethylsiloxy, dimethylpropylsiloxy, t-butyldimethylsiloxy, triethylsiloxy, triethoxysiloxy, tripropylsiloxy, tributoxysiloxy, dimethyloctylsiloxy, tributylsiloxy, trihexylsiloxy, triphenylsiloxy groups and the like.

The metal naphthalocyanine derivative represented by the above formula (I) generates charges by irradiation of light. That is, it exhibits photoconductivity. By utilizing this property, said metal naphthalocyanine derivative can be used as the organic photoconductive substance (charge generating substance) for electrophotographic plate. Thus, it can be used as the photoconductive layer of the electrophotographic plate comprising a film containing the metal naphthalocyanine derivative according to the present invention.

The electrophotographic plate according to the present invention comprises a photoconductive layer provided on an electroconductive support.

In the present invention, the photoconductive layer is a layer containing an organic photoconductive substance, and it may take any construction, for example, (i) a film of an organic photoconductive substance, (ii) a film containing an organic photoconductive substance and a binder, (iii) a complex double layer type comprising a charge generation layer and a charge transport layer, etc.

As the above organic photoconductive substance, the metal naphthalocyanine derivative represented by the above formula (I) can be used as the essential component, and further those known in the art can be used in combination therewith. Also, as the organic photoconductive substance, it is preferable to use the metal naphthalocyanine derivative represented by the above formula (I), optionally together with an organic pigment generating charges, and also to use a charge transport substance at the same time. In the complex double layer type described above, said metal naphthalocyanine derivative, optionally together with the organic pigment generating charges, is contained in the charge generation layer, while a charge transport substance is contained in the charge transport layer.

As the above organic pigment generating charges, there can be employed pigments known to generate charges, such as non-metal type pigment having various crystalline structures, including azoxybenzene type, disazo type, trisazo type, benzimidazole type, polycyclic quinone type, indigoid type, quinacridone type, perylene type, methine type, α-type, β-type, γ-type, δ-type, ε-type, χ-type, etc. or metal type such as phthalocyanine type, etc. These pigments are disclosed in, for example, Japanese Unexamined Patent Publications Nos. 37543/1972, 37544/1972, 18543/1972, 18544/1972, 43942/1973, 70538/1973, 1231/1974, 105536/1974, 75214/1975, 44028/1978 and 17732/1979.

Also, τ, τ', η and η' type non-metal phthalocyanines as disclosed in Japanese Unexamined Patent Publication No. 182640/1983 and European Unexamined Patent Publication No. 92,255 are available. Otherwise, all of organic pigments capable of generating charge carriers by photoirradiation can be used.

Examples of the above charge transport substance may include high molecular weight compounds such as poly-N-vinylcarbazole, halogenated poly-N-vinylcarbazole, polyvinylpyrene, polyvinyl indoloquinoxaline, polyvinylbenzthiophene, polyvinyl anthracene, polyvinyl acridine, polyvinyl pyrazoline, etc.; low molecular weight compounds such as fluorenone, fluorene, 2,7-dinitro-9-fluorenone, 4H-indeno(1,2,6)thiophene-4-one, 3,7-dinitrodibenzothiophene-5-oxide, 1-bromopyrene, 2-phenylpyrene, carbazole, N-ethylcarbazole, 3-phenylcarbazole, 3-(N-methyl-N-phenylhydrazone)methyl-9-ethylcarbazole, 2-phenylindole, 2-phenylnaphthalene, oxadiazole, 2,5-bis(4-diethylaminophenyl)-1,3-4-oxadiazole, 1-phenyl-3-(4-diethylaminostyryl)-5-(4-diethylaminostyryl)-5-(4-diethylaminophenyl)pyrazoline, 1-phenyl-3-(p-diethylaminophenyl)pyrazoline, p-(diethylamino)stilbene, 2-(4-dipropylaminophenyl)-4-(4-dimethylaminophenyl)-5-(2-chlorophenyl)-1,3-oxazole, 2-(4-dimethylaminophenyl)-4-(4-dimethylaminophenyl)-5-(2-fluorophenyl)-1,3-oxazole, 2-(4-diethylaminophenyl)-4-(4-dimethylaminophenyl)-5-(2-fluorophenyl)-1,3-oxazole, 2-(4-dipropylaminophenyl)-4-(4-dimethylaminophenyl)-5-(2-fluorophenyl)-1,3-oxazole, imidazole, chrysene, tetraphene, acridene, triphenylamine, derivatives of these, etc.

When a mixture of the above metal naphthalocyanine derivative or said metal naphthalocyanine derivative and an organic pigment generating charges and a charge transport substance is used, it is preferable to formulate the latter/the former at a proportion of 10/1 to 2/1 in terms of weight ratio. In this case, if the charge transport substance is a high molecular weight compound, no binder may be used. However, in this case or in the case of using a charge transport substance of a low molecular weight compound, it is preferable to use a binder in an amount of 500% by weight or less based on the total amount of these compounds. Also, when a low molecular weight compound is used as the charge transport substance, it is preferable to use a binder in an amount of 30% by weight or more based on the total amount of these compounds. Also, in the case of using no charge transport substance, a binder may be used in the same amount. When these binders are used, it is further possible to add additives such as plasticizers, flowability imparting agents, pinhole inhibiting agents, etc., if necessary.

In the case of forming a complex double layer type photoconductive layer comprising a charge generation layer and a charge transport layer, in the charge generation layer, the metal naphthalocyanine derivative or said derivative and an organic pigment generating charges together therewith is contained, and the binder may be contained in an amount of 500% by weight or less based on said organic pigment, and also the additives as mentioned above may be added in an amount of 5% by weight or less based on the amount of said metal naphthalocyanine derivative or the total amount of said derivative and the organic pigment. On the other hand, in the charge transport layer, the above charge transport substance is contained, and the binder may be contained in an amount of 500% by weight or less based on said charge transport substance. When the charge transport substance is a low molecular weight compound, the binder should be preferably contained in an amount of 50% by weight or more based on said compound. In the charge transport layer, the additives as mentioned above may be contained in an amount of 5% by weight or less based on the charge transport substance.

As the binder usable in all the cases as described above, there may be included silicone resin, polyamide resin, polyurethane resin, polyester resin, epoxy resin, polyketone resin, polycarbonate resin, polyacrylic resin, polystyrene resin, styrene-butadiene copolymer, polymethyl methacrylate resin, polyviny chloride, ethylene-vinyl acetate copolymer, vinyl chloride-vinyl acetate copolymer, polyacrylamide resin, polyvinyl carbazole, polyvinyl pyrazoline, polyvinyl pyrene, etc. Also, thermosetting resins and photocurable resins which can be crosslinked by heat and/or light can be also used.

Anyway, so long as resins are insulting and capable of forming films under ordinary state, and can be cured by heat and/or light to form films, there are no particular limitations. As the plasticizer, halogenated paraffins, dimethylnaphthalene, dibutylphthalate, etc. may be employed. As the flowability imparting agents, Modaflow (a trade name: manufactured by Monsanto Chemical Co.), Akulonal 4F (a trade name: manufactured by BASF Co.), etc. may be employed, while as the pinhole inhibiting agents, benzoin, dimethylphthalate, etc. may be employed. These can be used as suitably selected, and their amounts may be adequately determined.

In the present invention, the electroconductive support may be an electroconductive member comprising a paper or plastic film subjected to electroconductive treatment, a plastic film having a metal foil such as aluminum laminated thereon, a metal plate, etc.

The electrophotographic plate according to the present invention comprises a photoconductive layer formed on an electroconductive support. The thickness of the photoconductive layer should be preferably 5 to 50 μm. When the complex type of charge generation layer and charge transport layer is used as the photoconductive layer, the charge generation layer is made 0.001 to 10 μm thick, particularly preferably 0.2 to 5 μm thick. If it is less than 0.001 μm, the charge generation layer can be formed uniformly with difficulty, while if it exceeds 10 μm, the electrophotographic characteristics tend to be lowered. The thickness of the charge transport layer should be preferably 5 to 50 μm, particularly preferably 8 to 20 μm. With a thickness less than 5 μm, the initial potential will be lowered, while in excess of 50 μm, the sensitivity tends to be lowered.

For forming a photoconductive layer on an electroconductive support, there may be employed the method in which an organic photoconductive substance is vapor deposited on the electroconductive layer, and the method in which an organic photoconductive substance and other components, if necessary, are dissolved or dispersed in a ketone type solvent such as acetone, methyl ethyl ketone, etc., an ether type solvent such as tetrahydrofuran, etc., an aromatic solvent such as toluene, xylene, etc., a halogenated hydrocarbon type solvent such as methylene chloride, carbon tetrachloride, etc., an alcoholic solvent such as methanol, ethanol, propanol, etc. and applied on the electroconductive support, followed by drying. As the coating method, the spin coating method, the dipping method, etc. can be employed. Formation of the charge generation layer and the charge transport layer can be also similarly practiced, and in this case, either of the charge generation layer and the charge transport layer may be made the upper layer, and the charge generation layer may be also sandwiched between two charge transport layers.

When the above metal naphthalocyanine derivative is vacuum vapor deposited, it is preferable to heat said metal naphthalocyanine derivative under high vacuum of $10^{-5}$ to $10^{-6}$ mmHg. Also, when said metal naphthalocyanine derivative is coated by the spin coating method, it is preferable to perform spin coating at a rotational number of 3000 to 7000 rpm by use of a coating solution containing the naphthalocyanine compound represented by the formula (I) dissolved in a halogenated solvent or a non-polar solvent such as chloroform, toluene, etc. When coating is performed according to the dipping method, it is preferable to dip the electroconductive support in a coating liquid having the naphthalocyanine compound represented by the formula (I) dispersed in a polar solvent such as methanol, dimethylformamide by means of a ball mill, sonication, etc.

Formation of the protective layer may be practiced according to the same coating and drying method as in formation of the photoconductive layer.

The electrophotographic plate of the present invention can have further a thin adhesive layer or barrier layer formed immediately on the electroconductive layer, and may also have a protective layer on the surface.

In the following, synthesis examples of metal naphthalocyanine derivatives are shown.

Synthesis example 1

(1) Synthesis of dicyanonaphthalene:

To 0.1 mol of tetrabromoxylene were added 0.17 mol of fumaronitrile, 0.66 mol of sodium iodide and 400 ml of anhydrous dimethylformamide, and the mixture was stirred under heating at 70° to 80° C. for 7 hours. The reaction mixture was added to 800 g of ice-water, and to the resultant precipitate was added about 15 g of sodium hydrogen sulfite and the mixture was left to stand overnight. Subsequently, the mixture was filtered and dried, followed by recrystallization from chloroform/ethanol, to give white 2,3-dicyanonaphthalene. The yield was 80%.

(2) Synthesis of 1,3-diiminobenzisoindoline:

Into a mixture of 2.5 mol of 2,3-dicyanonaphthalene, 0.075 mol of sodium methoxide and one liter of methanol, ammonia gas was flowed at an appropriate flow rate for 40 minutes. Then, the reaction mixture was heated under reflux while passing ammonia gas therethrough for about 4 hours. After cooling, the product was filtered and recrystallized from a solvent mixture of methanol/ether to obtain yellow 1,3-diiminobenzisoindoline. The yield was 66%.

(3) Synthesis of dichlorogermaniumnaphthalocyanine:

A mixture of 3 mmol of 1,3-diiminobenzisoindoline, 4.8 mmol of germanium tetrachloride, 2 ml of dried tri-n-butylamine and 4 ml of dried tetralin was heated under reflux for about 2.5 hours. After cooling, 3 ml of methanol was added to the reaction mixture, and the mixture was left to stand and then filtered. The product was sufficiently washed with methanol to give dark green dichlorogermaniumnaphthalocyanine. The yield was 24%.

(4) Synthesis of dihydroxygermaniumnaphthalocyanine:

To 0.71 mol of dichlorogermaniumnaphthalocyanine was added 20 ml of conc. sulfuric acid and, after stirred at room temperature for 2 hours, the reaction mixture was added to 60 g of ice. Subsequently, after filtration and drying, the precipitate was added into 60 ml of 25% ammonia water, heated under reflux for one hour to obtain quantitatively dihydroxygermaniumnaphthalocyanine.

(5) Synthesis of bis(triethylsiloxy)germaniumnaphthalocyanine:

To 0.8 mmol of dihydroxygermaniumnaphthalocyanine were added 8 mmol of triethylsilyl chloride and 70 ml of β-picoline, and the mixture was heated under reflux for 1.5 hours. Subsequently, after filtration, the filtrate was added to a mixture of water/ethanol to effect precipitation. The precipitate was filtered, and then recrystallized from n-hexane to obtain the naphthalocyanine compound of the present invention. The yield was 50%.

The absorption spectrum ($CH_2Cl_2$ solution) is shown in FIG. 1.

The compound was found to have a melting point, elemental analysis values and NMR spectrum values as shown below.

(1) m.p. >300° C.;

(2) Elemental analysis values:

| | C | H | N |
|---|---|---|---|
| Calcd. (%) | 68.77 | 5.19 | 10.69 |
| Found (%) | 67.07 | 4.90 | 10.58 |

(3) NMR spectrum values ($CDCl_3$) δ values 10.14 (8H, S), 8.71 (8H, dd, J=3.05 Hz), 7.94 (8H, dd, J=3.05 Hz), −1.00 (12H, t, J=7.93 Hz), −2.02 (18H, q, J=7.93 Hz).

Synthesis example 2

Figure 2:
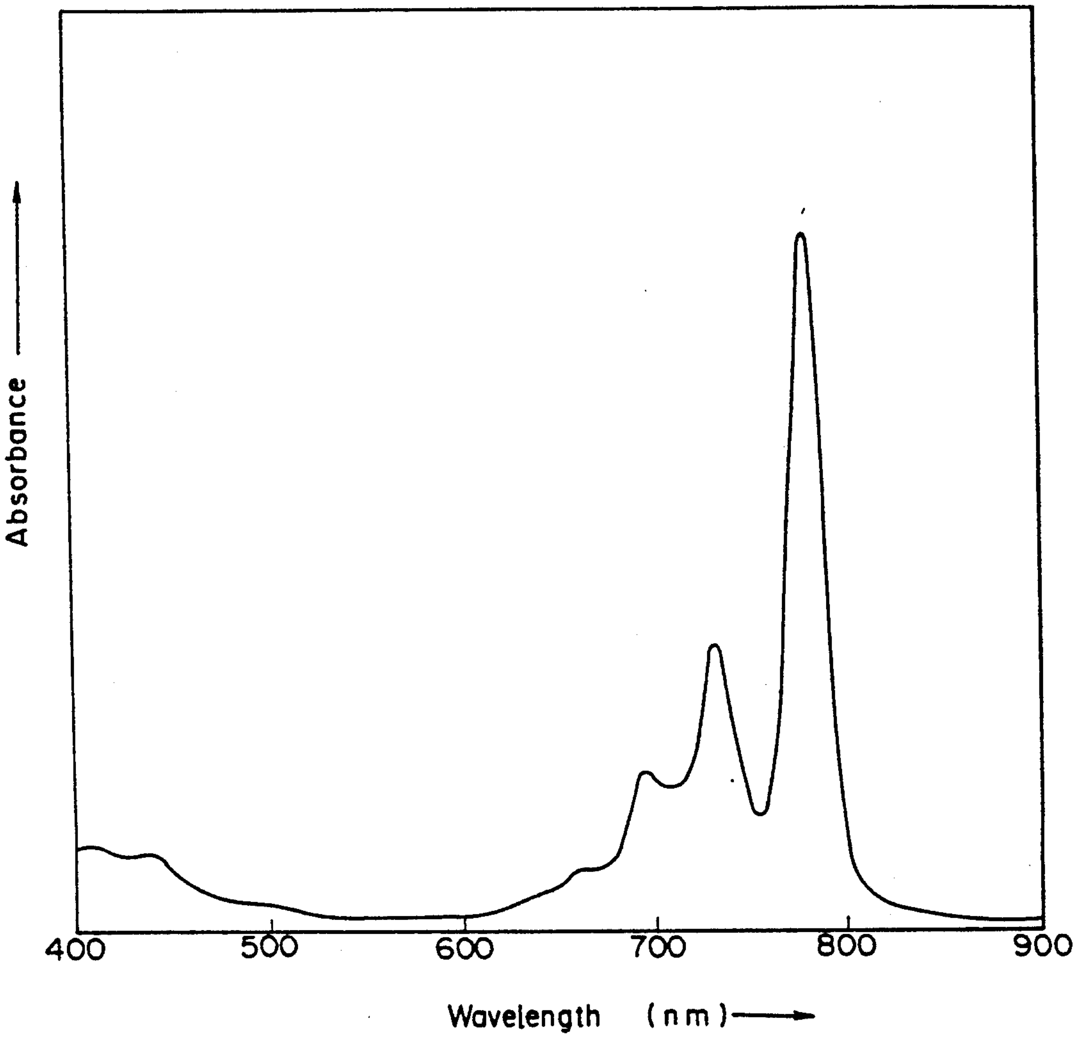
FIG. 2 is an absorption spectrum of the $CH_2Cl_2$ solution of the naphthalocyanine derivative synthesized in Synthesis example 2 wherein two tripropylsiloxy groups are bonded to germanium which is the center metal.

In (5) of Synthesis example 1, tripropylsilyl chloride was used in place of triethylsilyl chloride, following otherwise the same procedure as in Synthesis example 1, to prepare bis(tripropylsiloxy)germaniumnaphthalocyanine. The absorption spectrum ($CH_2Cl_2$ solution) is shown in FIG. 2.

Synthesis example 3

Figure 3:
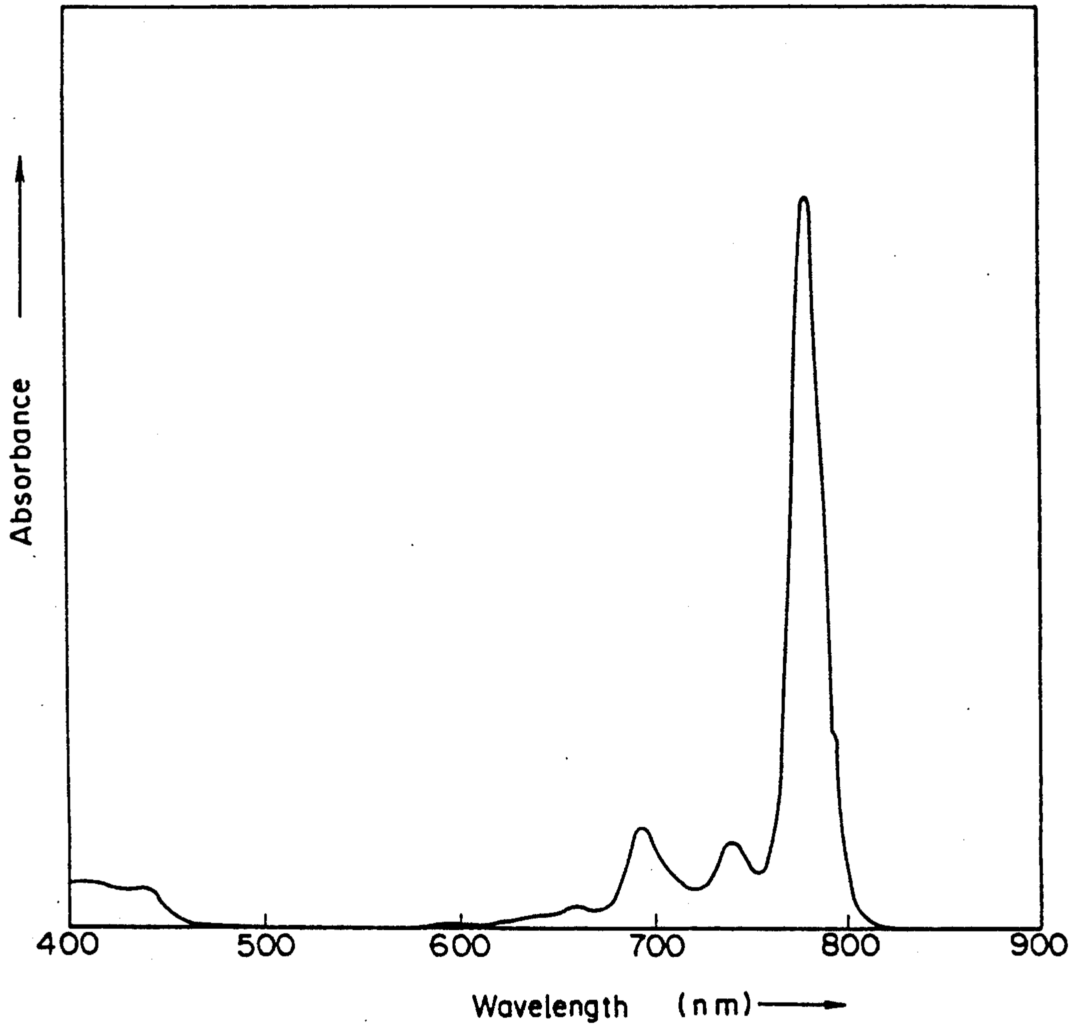
FIG. 3 is an absorption spectrum of the $CH_2Cl_2$ solution of the naphthalocyanine derivative synthesized in Synthesis example 3 wherein two tributylsiloxy groups are bonded to germanium which is the center metal.

In (5) of Synthesis example 1, tributylsilyl chloride was used in place of triethylsilyl chloride, following otherwise the same procedure as in Synthesis example 1, to prepare bis(tributylsiloxy)germaniumnaphthalocyanine. The absorption spectrum ($CH_2Cl_2$ solution) is shown in FIG. 3.

The compound was found to have a melting point, elemental analysis values and NMR spectrum values as shown below.

(1) m.p. >300° C.;

(2) Elemental analysis values:

| | C | H | N |
|---|---|---|---|
| Calcd. (%) | 71.10 | 6.46 | 9.21 |
| Found (%) | 71.03 | 6.41 | 9.41 |

Figure 6:
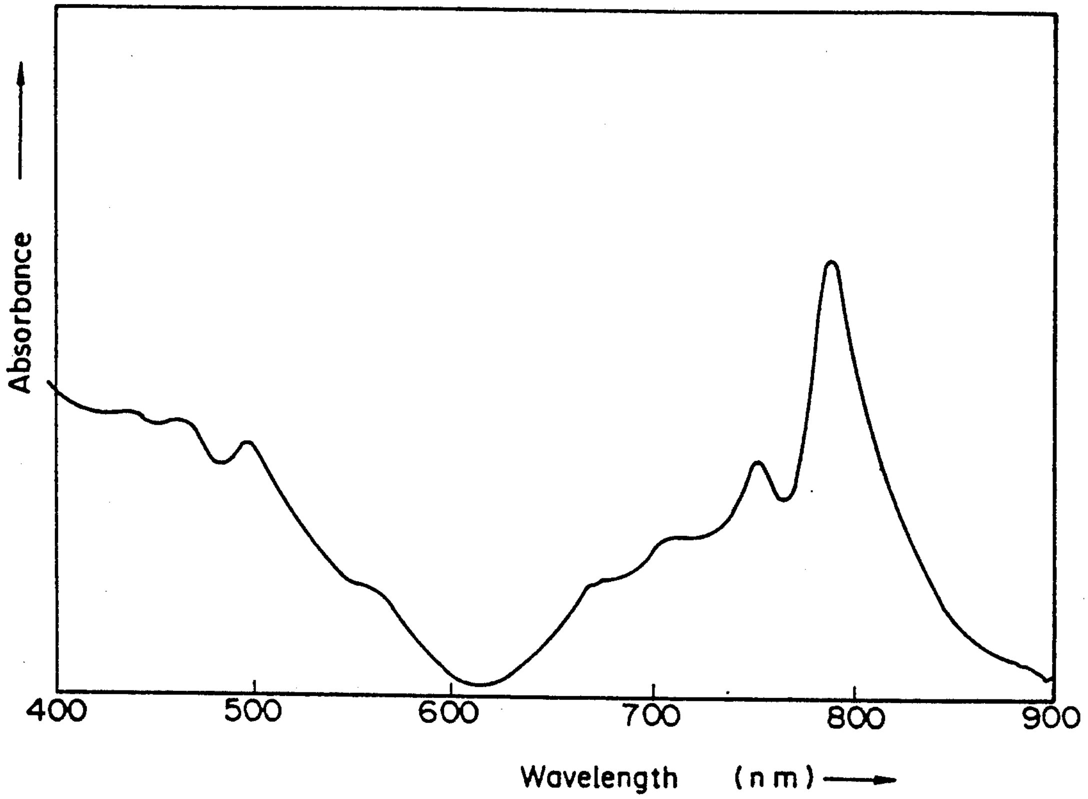
FIG. 6 is an absorption of spectrum of the $CH_2Cl_2$ solution of the naphthalocyanine derivative synthesized in Synthesis example 6 wherein two trihexylsiloxy groups are bonded to germanium which is the center metal.

(3) NMR spectrum values (NMR spectrum is shown in FIG. 6) ($CDCl_3$): δ values 10.12 (8H, S), 8.68 (8H, dd, J=6.10, 3.05 Hz), 7.94 (8H, dd, J=6.10, 3.35 Hz), −0.1—0.1 (30H, m), −0.89 (12H, quintet, J=7.63 Hz), −1.99 (12H, J=7.63 Hz).

Synthesis example 4

Figure 4:
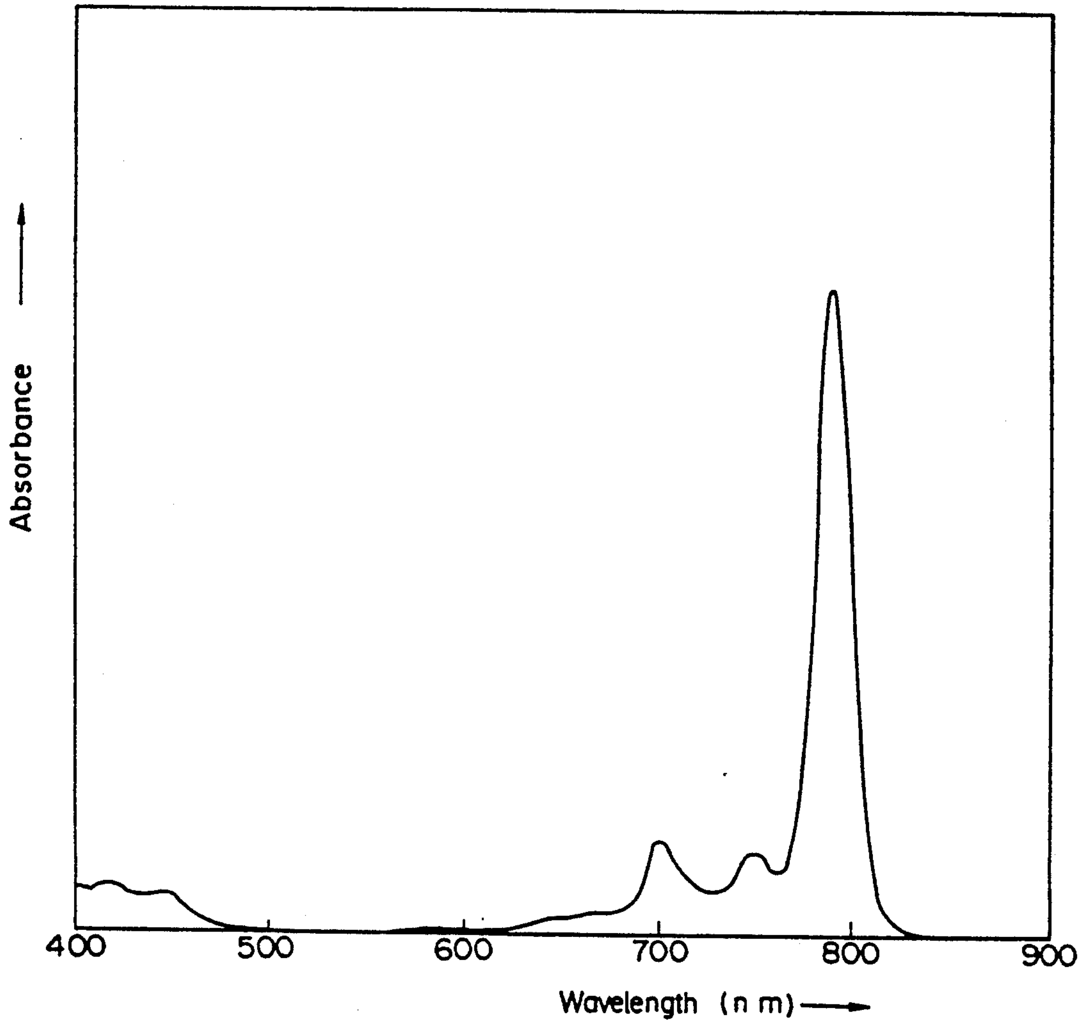
FIG. 4 is an absorption spectrum of the $CH_2Cl_2$ solution of the naphthalocyanine derivative synthesized in Synthesis example 4 wherein two triphenylsiloxy groups are bonded to germanium which is the center metal.

In (5) of Synthesis example 1, triphenylsilyl chloride was used in place of triethylsilyl chloride, following otherwise the same procedure as in Synthesis example 1, to prepare bis(triphenylsiloxy)germaniumnaphthalocyanine. The absorption spectrum ($CH_2Cl_2$ solution) is shown in FIG. 4.

Synthesis example 5

1,3-Diiminobenzisoindoline was synthesized according to Synthesis example 1.

(6) Synthesis of dichlorotinnaphthalocyanine:

A mixture of 3 mmol of 1,3-diiminobenzisoindoline, 4.8 mmol of stannic chloride, 2 ml of dried tri-n-butylamine and 4 ml of dried tetraline was heated under reflux for about 2.5 hours. After cooling, 3 ml of methanol was added to the reaction mixture, and after left to stand, the mixture was filtered and sufficiently washed with methanol to obtain dark green dichlorotinnaphthalocyanine. The yield was 24%.

(7) Synthesis of dihydroxytinnaphthalocyanine:

To 0.71 mmol of dichlorotinnaphthalocyanine was added 20 ml of conc. sulfuric acid and after stirring at room temperature for 2 hours, the reaction mixture was added to 60 g of ice. Subsequently, after filtration and drying, the precipitate was added into 60 ml of 25% ammonia water and heated under reflux for one hour to obtain quantitatively dihydroxytinnaphthalocyanine.

Figure 5:
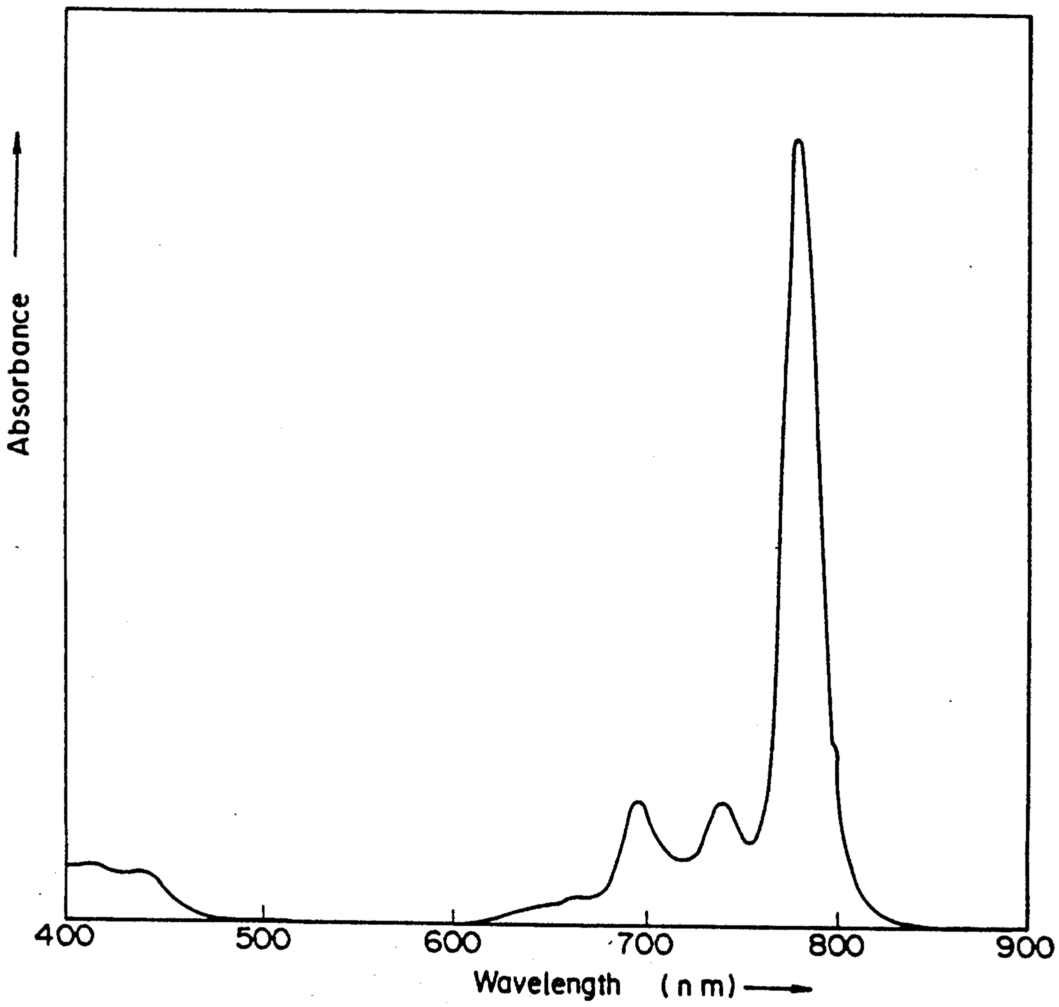
FIG. 5 is an absorption spectrum of the $CH_2Cl_2$ solution of the naphthalocyanine derivative synthesized in Synthesis example 5 wherein two triethylsiloxy groups are bonded to tin which is the center metal.

(8) Synthesis of bis(triethylsiloxy)tinnaphthalocyanine:

To 0.8 mmol of dihydroxytinnaphthalocyanine were added 8 mmol of triethylsilyl chloride and 70 ml of β-picoline, and the mixture was heated under reflux for 1.5 hours. Subsequently, after filtration, the filtrate was added to a mixture of water/ethanol to effect precipitation. The precipitate was filtered and recrystallized from n-hexane to obtain the naphthalocyanine compound according to the present invention. The yield was 50%. The absorption spectrum ($CH_2Cl_2$ solution) is shown in FIG. 5.

Synthesis example 6

In (5) of Synthesis example 1, trihexylsilyl chloride was used in place of triethylsilyl chloride, following otherwise the same procedure as in Synthesis example 1, to synthesize bis(trihexylsiloxy)germaniumnaphthalocyanine. The absorption spectrum ($CH_2Cl_2$ solution) is shown in FIG. 6.

Reference example 1

Figure 7:
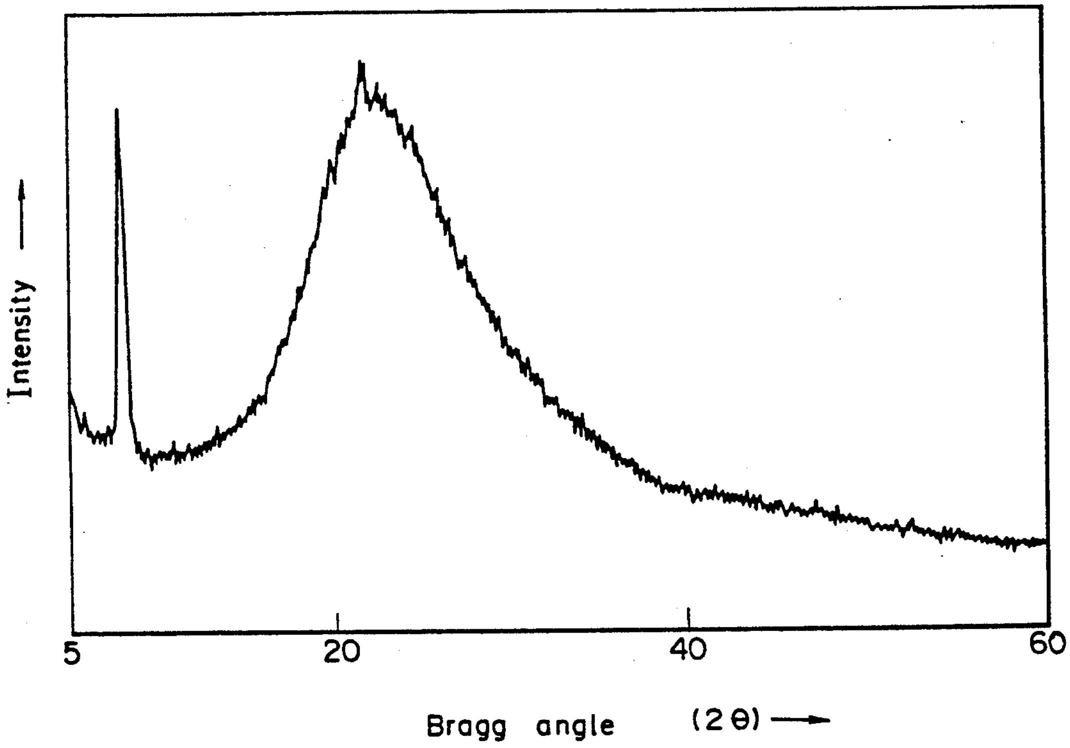
FIG. 7 is an X-ray diffraction chart of the film with a thickness of 40 nm of the naphthalocyanine derivative synthesized in Synthesis example 3 wherein two tributylsiloxy groups are bonded to germanium which is the center metal (Reference example 1)
Figure 8:
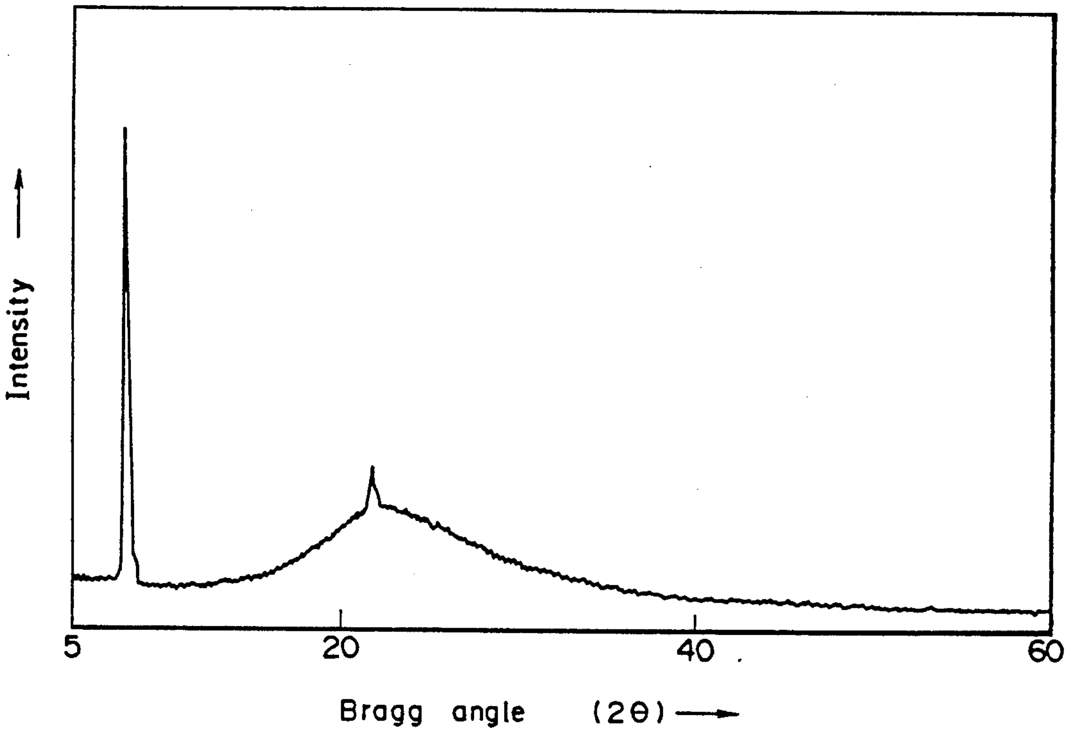
FIG. 8 is an X-ray diffraction chart of the film with a thickness of 100 nm of the naphthalocyanine derivative synthesized in Synthesis example 3 wherein two tributylsiloxy groups are bonded to germanium which is the center metal (Reference example 1)

The naphthalocyanine derivative of the formula (I) synthesized in Synthesis example 3 wherein M is germanium and L and L' are both tributylsiloxy groups was vapor deposited under vacuum of $1\times10^{-5}$ mmHg on a glass substrate according to the resistance heating method. FIG. 7 shows the X-ray diffraction chart of the film with a film thickness of 40 nm. Also, FIG. 8 shows the X-ray diffraction chart of a film with a thickness of 100 nm. Even when the same derivative may be vapor deposited under the same conditions, the crystalline structure of the film can be varied by varying the film thickness, whereby the characteristics depending on the film structure can be varied as desired.

Figure 9:
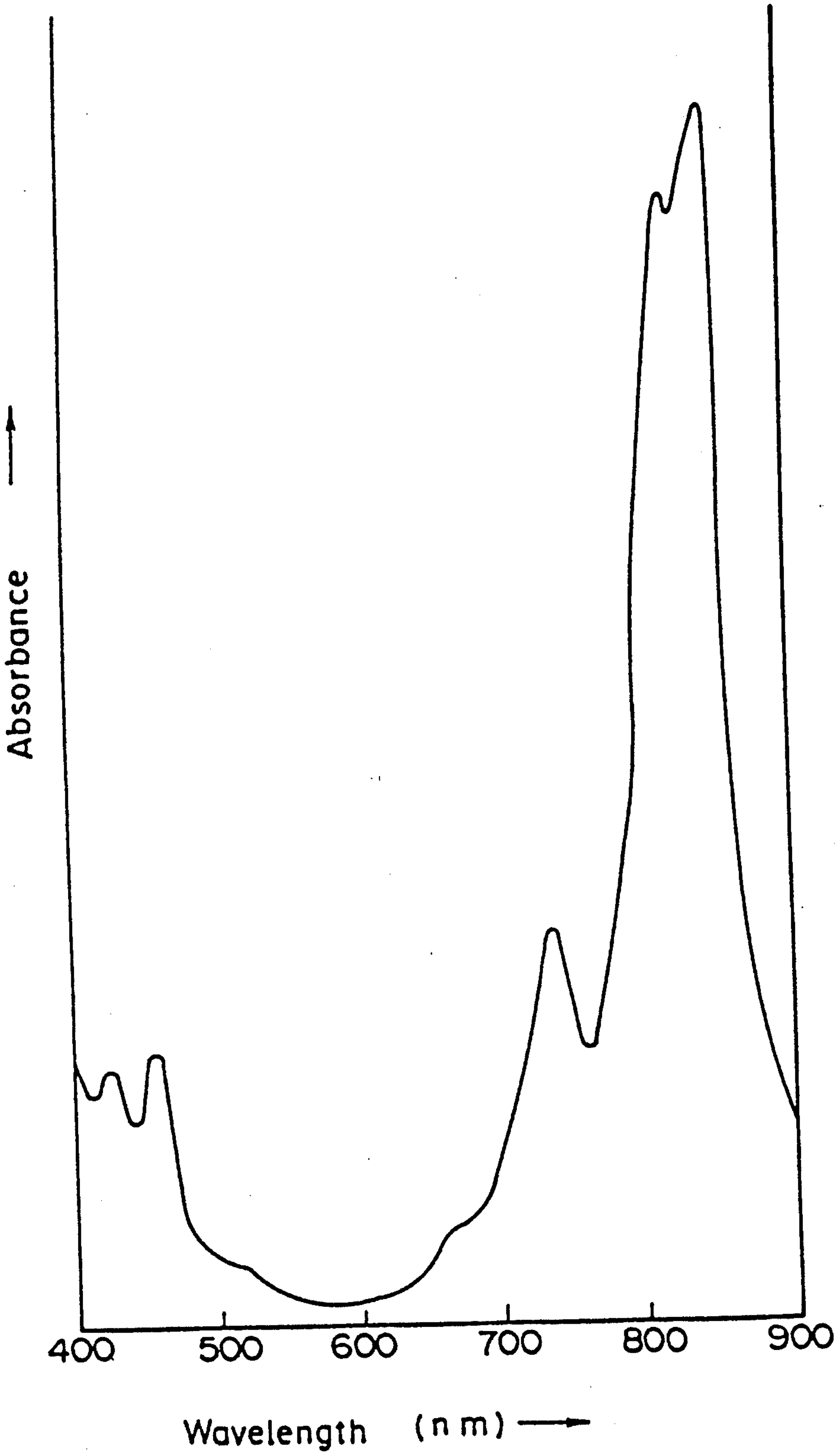
FIG. 9 is an absorption spectrum of the film with a thickness of 40 nm of the naphthalocyanine derivative synthesized in Synthesis example 3 wherein two tributylsiloxy groups are bonded to germanium which is the center metal (Reference example 1)
Figure 10:
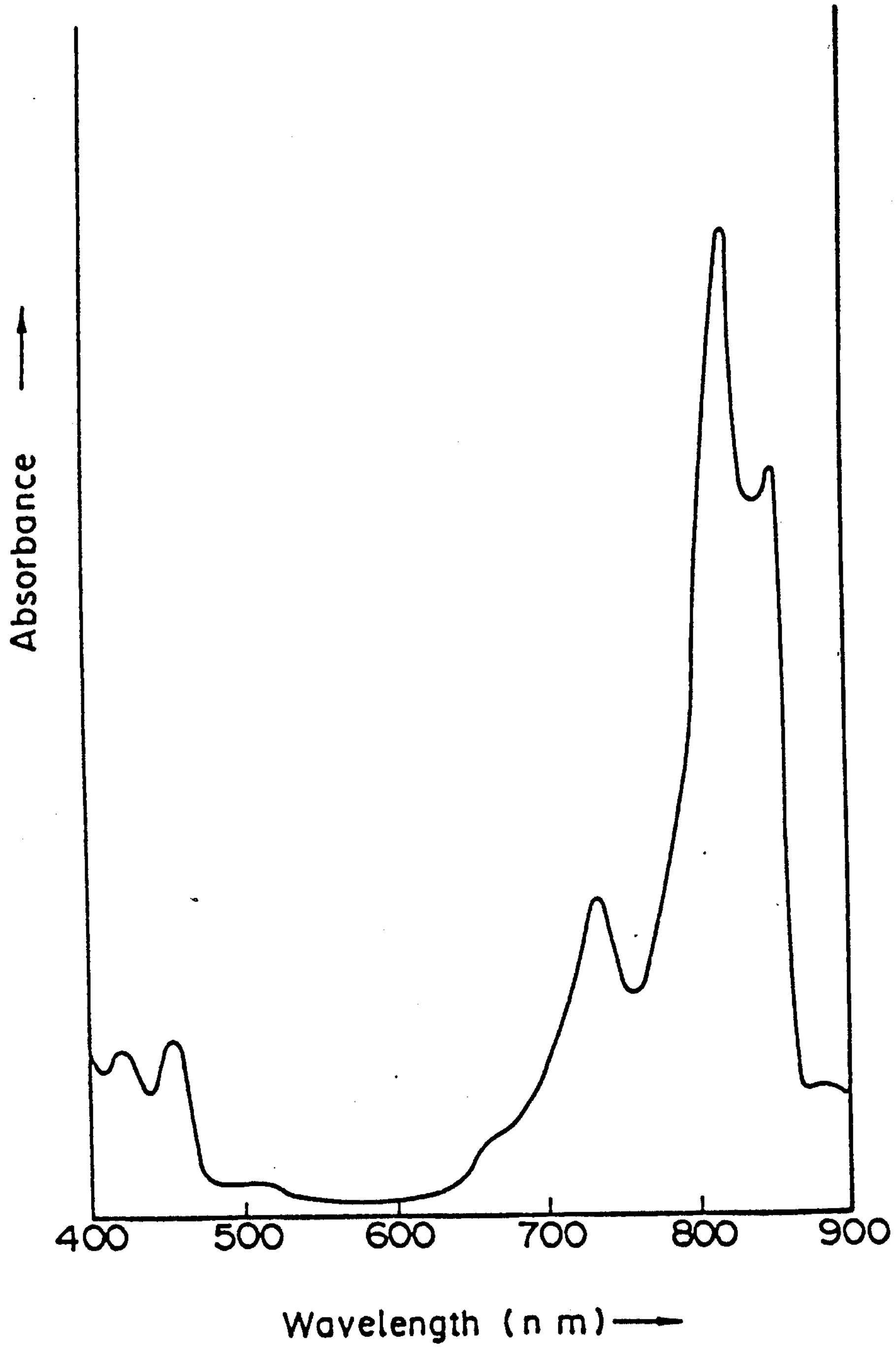
FIG. 10 is an absorption spectrum of the film with a thickness of 100 nm of the naphthalocyanine derivative synthesized in Synthesis example 3 wherein two tributylsiloxy groups are bonded to germanium which is the center metal (Reference example 1).

FIG. 9 and FIG. 10 show the absorption spectra of the above films with the film thicknesses of 40 nm and 100 nm, respectively. By change in film thickness, the intensity ratio of the two peaks on the longer wavelength side can be changed.

EXAMPLE 1

The naphthalocyanine compound of the formula (I) synthesized in Synthesis example 1 wherein M is germanium and L and L' are both triethylsiloxy groups was vapor deposited under vacuum of $2\times10^{-5}$ mmHg to a thickness of 300 nm on an aluminum vapor deposition substrate according to the resistance heating method to form a charge generation layer comprising the film of said naphthalocyanine compound.

By use of a coating solution obtained by dissolving 5 g of 1-phenyl-3-(p-diethylaminostyryl)-5-(p-diethylaminophenyl)pyrazoline and 10 g of a polycarbonate resin in 85 g of a 1:1 solvent mixture of methylene chloride and 1,1,2-trichloroethane, the charge generation layer on the above substrate was coated by dipping with said solution, and the coating was dried at 120° C. for 30 minutes to form a charge transport layer with a thickness of 15 μm. By means of an electrostatic charging tester (produced by Kawaguchi Denki), the above electrophotographic plate was charged negatively by corona charging of 5 KV. Then, by use of a halogen lamp as the external light source, the light was irradiated as the monochromatic light by means of a monochrometer (manufactured by Ritsu Oyo Kogaku), whereby optical decay of the surface potential of said electrophotographic plate was measured.

As the result, when a monochromatic light of 800 nm in the near infra-red region was employed, the half reduction exposure dose (the product of the time period during which the residual potential becomes ½ and the light intensity) was 20 mJ/$m^2$.

EXAMPLE 2

The naphthalocyanine compound of the formula (I) synthesized in Synthesis example 2 wherein M is germanium and L and L' are tripropylsiloxy groups was vacuum vapor deposited in the same manner as in Example 1 to form a charge generation layer.

By use of a coating solution obtained by dissolving 5 g of 1-phenyl-3-(p-diethylaminostyryl)-5-(p-diethylaminophenyl)pyrazoline and 10 g of a polycarbonate resin in 85 g of a 1:1 solvent mixture of methylene chloride and 1,1,2-trichloroethane, the charge generation layer on the above substrate was coated by dipping with said solution, and the coating was dried at 120° C. for 30 minutes to form a charge transport layer with a thickness of 15 μm.

For the electrophotographic plate thus obtained, the half reduction exposure dose was measured by use of a monochromatic light of 800 nm in the near infra-red region in the same manner as in Example 1 and was found to be 15 mJ/m$^2$.

EXAMPLE 3

A charge generation layer and a charge transport layer were prepared in the same manner as in Example 1 except for using the naphthalocyanine compound of the formula (I) synthesized in Synthesis example 3 where M is germanium and L and L' are tributylsiloxy groups, and the half reduction exposure dose was measured by use of a monochromatic light of 800 nm in the near infra-red region in the same manner as in Example 1 to be 25 mJ/m$^2$.

EXAMPLE 4

A charge generation layer and a charge transport layer were prepared in the same manner as in Example 1 except for using the naphthalocyanine compound of the formula (I) synthesized in Synthesis example 4 where M is germanium and L and L' are triphenylsiloxy groups, and the half reduction exposure dose was measured by use of a monochromatic light of 800 nm in the near infra-red region in the same manner as in Example 1 and was found to be 30 mJ/m$^2$.

EXAMPLE 5

A charge generation layer and a charge transport layer were prepared in the same manner as in Example 1 except for using the naphthalocyanine compound of the formula (I) synthesized in Synthesis example 5 where M is tin and L and L' Ls are triethylsiloxy groups, and the half reduction exposure dose was measured by use of a monochromatic light of 800 nm in the near infra-red region in the same manner as in Example 1 was found to be 25 mJ/m$^2$.

EXAMPLE 6

A charge generation layer and a charge transport layer were prepared in the same manner as in Example 1 except for using the naphthalocyanine compound of the formula (I) synthesized in Synthesis example 6 where M is germanium and L and L' are trihexylsiloxy groups, and the half reduction exposure dose was measured by use of a monochromatic light of 800 nm in the near infra-red region in the same manner as in Example 1 and was found to be 3000 mJ/m$^2$.

The film containing the metal naphthalocyanine derivative has high sensitivity to light and electricity, and applicable for electrophotographic plate by utilizing this property, and the electrophotographic plate according to the present invention exhibits great absorption at around 800 nm and has the characteristic exhibiting high sensitivity to the longer wavelength region without treatment with a shifting agent, and therefore can exhibit excellent effect particularly when used in a laser beam printer, and also can be used for not only the laser printer as mentioned above, but also for facsimile or a printer by use of LED as the light source.

We claim:

1. A naphthalocyanine compound represented by the formula:

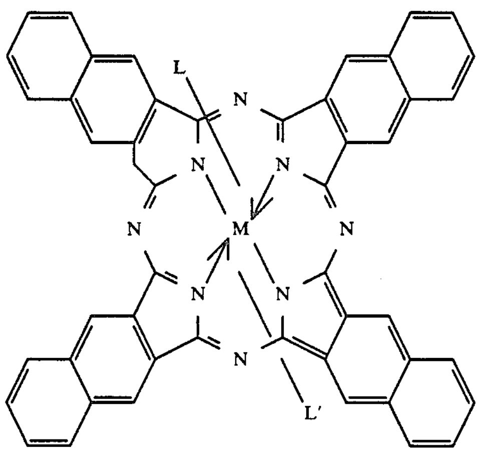

(I)

wherein M represents germanium or tin; L and L' each independently represent a siloxy group of the formula $R_1R_2R_3SiO$-wherein $R_1$, $R_2$ and $R_3$ each independently represent an alkyl group having 1 to 4 carbon atoms.

2. The naphthalocyanine compound according to claim 1, wherein $R_1$, $R_2$ and $R_3$ are the same.

3. The naphalocyanine compound according to claim 1, wherein M is germanium.

4. The naphthalocyanine compound according to claim 2, wherein M is germanium.

5. The naphthalocyanine compound according to claim 1, wherein M is tin.

6. The naphthalocyanine compound according to claim 2, wherein M is tin.

7. The naphthalocyanine compound according to claim 1, which is bis(triethylsiloxy)germaniumnaphthalocyanine.

8. The naphthalocyanine compound according to claim 1, which is bis(tripropylsiloxy)germaniumnaphthalocyanine.

9. The naphthalocyanine compound according to claim 1, which is bis(tributylsiloxy)germaniumnaphthalocyanine.

10. The naphthalocyanine compound according to claim 1, which is bis(triethylsiloxy)tinnaphthalocyanine.

* * * * *